United States Patent [19]

Pettit et al.

[11] Patent Number: 5,328,929
[45] Date of Patent: Jul. 12, 1994

[54] ISOLATION AND STRUCTURE OF SPONGISTATIN 2, SPONGISTATIN 3, SPONGISTATIN 4 AND SPONGISTATIN 6

[75] Inventors: George R. Pettit, Paradise Valley; Zbigniew A. Cichacz; Cherry L. Herald, both of Tempe, all of Ariz.

[73] Assignee: Arizona Board of Regents, Tempe, Ariz.

[21] Appl. No.: 86,668

[22] Filed: Jul. 2, 1993

[51] Int. Cl.⁵ .................. C01D 307/77; A01N 43/12
[52] U.S. Cl. .................. 514/462; 549/343; 549/344
[58] Field of Search ............... 549/344, 343; 514/462

[56] References Cited

U.S. PATENT DOCUMENTS

| | | | |
|---|---|---|---|
| Re. 29,163 | 3/1977 | Becher et al. | 549/344 |
| 4,199,515 | 4/1980 | Yamagishi et al. | 549/343 |
| 4,929,638 | 5/1990 | Dutton et al. | 514/450 |
| 5,064,855 | 11/1991 | Cullen et al. | 549/343 |
| 5,064,856 | 11/1991 | Garrity et al. | 514/462 |
| 5,095,127 | 3/1992 | Goudie et al. | 549/343 |
| 5,096,905 | 3/1992 | Kretzschmar et al. | 514/252 |
| 5,206,263 | 4/1993 | Dirlam et al. | 514/460 |
| 5,217,993 | 6/1993 | O'Doherty | 514/459 |

Primary Examiner—C. Warren Ivy
Assistant Examiner—Raymond Covington
Attorney, Agent, or Firm—Richard R. Mybeck

[57] ABSTRACT

A black Spongia sp. in the Porifera class Demospongiae has been found to contain two new and exceptionally active cell (human cancer) growth inhibitors named spongistatin 2 and spongistatin 3. A bright colored Southwest Indian Ocean sponge *Spirastrella spinispirulifera* has also been found to contain related human cancer cell growth inhibitors named spongistatin 4 and spongistatin 6. A method of treating human cancer cells with spongistatin 1, spongistatin 2, spongistatin 3, spongistatin 4 and spongistatin 6 is also disclosed. The approximate mean $GI_{50}$ of the disclosed compounds in the NCI cell line panel is about $10^{-10}$ µg/ml.

9 Claims, No Drawings

ISOLATION AND STRUCTURE OF SPONGISTATIN 2, SPONGISTATIN 3, SPONGISTATIN 4 AND SPONGISTATIN 6

The present invention relates to the discovery and isolation of four new structurally related compositions of matter. Two of these compounds are constituents of an Eastern Indian Ocean marine sponge of the genus Spongia herein denominated as "spongistatin 2" and "spongistatin 3". Two other compounds were extracted from the marine sponge *Spirastrella spinispirulifera* (Class Demospongiae, Order Hadromerida, Family Spirastrellidae). These compounds are denominated herein as "spongistatin 4" and "spongistatin 6". The new macrocyclic lactones were found to be remarkably potent and specific against the human cancer cell lines in the U.S. National Cancer Institute's panel. Some of the work described herein was supported by NCI Grant 01G CA-44344-01-04. The United States government may have certain rights to this invention.

BACKGROUND OF THE INVENTION

A great number of ancient marine invertebrate species in the Phyla Bryozoa, Mollusca and Porifera were well established in the earth's oceans over one billion years ago. Certainly such organisms have explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least that time period. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and-/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types, that would have eluded discovery by contemporary techniques of medicinal chemistry. Fortunately, some of these expectations have been realized in the intervening period. Illustrative of these successes are the discoveries of the bryostatins, dolastatins, and cephalostatins by the Cancer Research Institute in Tempe, Ariz. where several members of these series of remarkable anticancer drug candidates are either now in human clinical trial or preclinical development. See: U.S. Pat. Nos. 4,816,444, 4,833,257, 4,873,245, and 4,879,278.

As is well known to those presently engaged in medical research, the time between the isolation of a new compound, and its introduction to the market place, is at least several years in the best case and can be several decades. Consequently, industry, in association with the government, has devised a number of qualifying tests which serve two purposes. One purpose is to eliminate those substances whose results in the qualifiers unequivocally demonstrate that the further expenditure of funds on developing those substances would be economically counter-productive. The second, and more important purpose, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars ($10,000,000 U.S.) per substance. Economics dictate that such an investment not be made unless there is a reasonable likelihood that it can be recovered. Absent such an opportunity, there will be no such investment, and without investment, the research requisite for the discovery of potentially life saving drugs will stop.

Only two hundred years ago, many diseases ravaged humankind. Many of these diseases now have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated in the United States by the National Cancer Institute (NCI). NCI, as a government entity, has been charged with assisting anti-cancer research. To establish whether a substance has anti-cancer activity, NCI has established a variety of protocols, one of which involves testing the candidate substance against a cell line panel containing 60 human tumor cell lines. This protocol has been verified and is generally accepted throughout the scientific community. This protocol and the established statistical means of evaluating the results obtained therefrom have been fully described in the literature. See *Principles & Practice of Oncology* PPO Updates, Volume 3, Number 10, October 1989, by Michael R. Boyd, M.D., Ph.D., for an in depth description of the test protocol. The statistical analysis is explained in "Display and Analysis of Patterns of Differential Activity of Drugs Against Human Tumor Cell Lines: Development of Means Graph and COMPARE Algorithm" *Journal of the National Cancer Institute* Reports Vol. 81, No. 14, Pg. 1088, Jul. 14, 1989, by K. D. Paull et al. Both of these references are incorporated herein by this reference thereto. The effectiveness and validity of the NCI in vitro protocol continues to be verified.

Two newer references of note have been authored, in whole or in part by Dr. M. R. Boyd of the National Cancer Institute. The first is "Data Display and Analysis Strategies from the NCI disease Oriented in vitro Antitumor Drug Screen." Boyd, M. R. et al, in *Cytotoxic Anticancer Drug Models and Concepts for Drug Discovery and Development*; Valeriote, F. A., Corbett, T., Baker, L. Eds; Kluwer Academic Press: Amsterdam, 1992, pp11-34. The second is "The Future of New Drug Development." Boyd, M. R. in *Current Therapy in Oncology*; Niederhuber, J. E., Ed. Mosby: St. Louis, 1993, pp11-22.

These articles establish that those skilled in the art believe that in vitro screens are the primary method by which new antineoplastic compositions will be discovered. Progress has been sorely lacking in treating many kinds of cancer because effective anti-neoplastic compositions for these cancers have not been discovered. Plainly, the public interest is best served by maximizing, within Constitutional limits, the rewards for discovering a composition which is demonstrated to be effective in standard screening tests.

The Constitution of the United States (Art. 1, Sec. 8) authorizes Congress to establish the United States Patent and Trademark Office (USPTO) to promote scientific advancement. This obligation can only be fully met when the USPTO accepts current medical and scientific realities in the area of medical research.

The Framers of the Constitution meant to advance scientific advancement. Cells are alive. The impairment of human tumor cell growth is utility. The sole right obtained from the grant of Letters Patent is the right to prevent others from exploiting the subject matter of the patent. The recognition of cell line data as a measure of antineoplastic activity and therefore an acceptable showing of "utility" can only aid research in the United States, and thereby save the citizens of the United States from being held hostage by foreign governments or foreign corporations, if such research is no longer viable in the United States.

A major component of vigorous efforts for over two decades has been directed at marine sponge antineoplastic and/or cytotoxic biosynthetic products and it is toward the furtherance of that effort that the present invention is directed.

BRIEF SUMMARY OF THE INVENTION

Marine animal constituents of the macrocyclic lactone type, are proving to be exceptionally important sources of new anticancer drug candidates. Illustrative are current human clinical trials of bryostatin 1 and the advancing preclinical development of halichondrin B, halistatin 1 and ecteinascidin 729. Seven interesting (and cytotoxic) perhydropyrans of the onnamide series (from a Theonella species of marine sponge) and 13-deoxytedanolide, a cytotoxic macrocyclic lactone, from *Mycale adhaerens* (Porifera) are descriptive of related advances.

Spongistatin 1, described in applicant's co-pending application Ser. No. 08/006,279 was discovered in an Indian Ocean Spongi sp (family Spongiidae, class Demospongiae) and represents one of the most extraordinarily potent substances presently known against a subset of highly chemoresistant tumor types in the U.S. National Cancer Institute (NCI) panel of 60 human cancer cell lines. Intensive investigation of other active (P388 lymphocytic leukemia cell line bioassay) fractions from the same sponge species has revealed the presence of two new and exceptionally potent (NCI panel) macrocyclic lactones designated spongistatin 2 and 3. A synopsis of the isolation, structural elucidation and human cancer cell line activity of spongistatin 2 and spongistatin 3 is shown below.

The cell growth inhibitory (P388 leukemia) dichloromethane fraction prepared from a 400 kg (wet wt) scaleup recollection (1988) of Spongia sp conducted in the Republic of Maldives was separated by a series of steric exclusion and partition chromatographic steps employing SEPHADEX LH-20 to obtain P388 active fractions reminiscent of spongistatin 1. A careful HPLC sequence using C-8 SILICA GEL (PREPEX and ULTREMEX) and 1:1 methanol water to 5:5:8 methanol-acetonitrile-water afforded 4.34 mg ($1.08 \times 10^{-6}\%$ yield) of amorphous spongistatin 2: mp 140°–141° C.; $[\alpha]_D + 24.5°$, (C 0.39, $CH_3OH$); UV ($CH_3OH$, log $\epsilon$) $\lambda$, 220 (4.21), $\lambda$, 273 (2.95) nm; IR (film) 3426, 2937, 1736, 1651, 1603, 1381, 1234, 1177, 1086 $cm^{-1}$, high resolution FABMS m/z 1227.6040 $[M+K]^+$ corresponding to $C_{63}H_{96}O_{21}K$ (calcd mass 1227.6082). In contrast to that of spongistatin 1, no $[M-35]^+$ ion was found. Spongistatin 3 was also obtained (2.69 mg, $6 \times 10^{-8}\%$ yield) as a colorless and noncrystalline powder; mp 148°–149° C.; $[\alpha]_D + 28.1°$ (c 0.15, $CH_3OH$); UV ($CH_3OH$, log $\epsilon$) $\lambda$, 226 (3.14), $\lambda268$ (2.24) nm; IR (film) 3426, 2934, 1734, 1653, 1591, 1387, 1231, 1173, 1090 $cm^{-1}$; HRFAB ms, m/z 1219.5556 $[M+K]^+$ corresponding to $C_{61}H_{93}ClO_{20}K$ (calcd mass 1219.5584).

The typically bright colored (reds, purples) marine sponges of the genus Spirastrella (Class Demospongiae, Order Hadromerida, Family Spirastrellidae) have not heretofore been examined for biologically active constituents except for the arsenic content of *S. insignis*. In 1973 a 20 year investigation of antineoplastic constituents in *Spirastrella spinispirulifera* collected off the Southeast Coast of Africa was begun. The isolation and structure of two remarkably potent antineoplastic substances from this sponge designated spongistatin 4 and spongistatin 6 is disclosed. Because spongistatin 4 and spongistatin 6 each proved to be only a trace ($10^{-7}\%$ yield) constituent, their isolation and structural elucidation was especially difficult and protracted. A synopsis now follows.

Increasingly larger (to 360 kg) recollections of *Spirastrella spinispirulifera* and chemical/biological research over the period to 1980 proved inadequate. By that time all effort was focused on a 2,409 kg sponge recollection preserved in ethanol that led to the discovery (the first few $\mu$gs of spongistatin 4 was isolated in September, 1982) of macrocyclic lactone. A murine P388 lymphocytic leukemia (PS system) active dichloromethane fraction prepared from the alcohol extract was initially separated by HPLC employing a unique pilot plant scale high-performance liquid chromatography (HPLC) system (SILICA GEL, $3 m \times 0.15 m$ column at 150 psi). Bioassay (PS) directed separation was continued using a series of SEPHADEX LH-20 (gel permeation and partition) and HPLC (MERCK RP-2 SILICA GEL with methanol-water gradients, PREPEX RP-8 with acetonitrile-water and finally LICHROSPHER 100 RP-18 with acetonitrile-water) to afford 10.7 mg ($4.4 \times 10^{-7}\%$, PS $ED_{50} 4.9 \times 10^{-5}$ $\mu$g/ml) of colorless spongistatin 4; mp 153°–154° C.; $[\alpha]^{22}D + 23.0°$ (c $= 0.19$, $CH_3OH$); UV ($CH_3OH$) $\lambda_{max}$ 229 nm, $\epsilon 170790$; IR (film) 3435, 2938, 1736, 1643, 1593, 1385, 1258, 1177, 1086, 993 $cm^{-1}$ high resolution FABMS, m/z 1219.5546 $[M+K]^+$ corresponding to $C_{61}H_{93}ClO_{20}K$ (calcd mass 1219.5586).

Similarly, murine P388 lymphocytic leukemia bioassay of a SEPHADEX LH-20 partition chromatographic fraction prepared from a 2,409 kg recollection of the Southwest (Africa) Indian Ocean sponge *Spirastrella spinispirulifera* (Carter, 1879) and final separation by HPLC (MERCK LICHROSPHER 100 RP-18) with 45% acetonitrile in water led to isolation of colorless spongistatin 6 (8.4 mg, $3.5 \times 10^{-7}\%$ yield): P388 $ED_{50} 3.4 \times 10^{-3}$ $\mu$g/ml; mp 139°–140° C.; $[\alpha]_{D22} + 22.0$ (c, 0.16, $CH_3OH$); UV ($CH_3OH$) $\lambda_{max}$ 223 nm (log $\epsilon 4.27$); IR (film) 3431, 2938, 1736, 1645, 1603, 1387, 1256, 1175, 1086, 993 $cm^{-1}$ HRFAB MS m/z 1185.5926 $[M+K]^+$, calcd for $C_{61}H_{94}O_{20}K$ 1185.5922.

Accordingly, the principal object of the present invention is the isolation of structurally unprecedented macrocyclic lactones herein denominated "spongistatin 2", "spongistatin 3", "spongistatin 4" and "spongistatin 6" each having a log molar TGI50 of less than log-10 against various human cancer cell lines.

Another object of the present invention is to obtain the structural elucidation of the substances herein denominated "spongistatin 2", "spongistatin 3", "spongistatin 4" and "spongistatin 6".

A further object of the present invention is to determine a method of treating human cells afflicted with an NCI cell line human cancer, with "spongistatin 1", "spongistatin 2", "spongistatin 3", "spongistatin 4" and "spongistatin 6".

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENTS

Isolation of Spongistatin 2 and Spongistatin 3

Processing began with the removal of the shipping solution (methanol/sea water) from the Spongia and its partitioning with dichloromethane by the counter-current method. The dichloromethane fraction was evaporated to give a black solid (472.0 g; PS $ED_{50}$ 0.91 µg/ml). The containers were refilled with 1:1 dichloromethane/methanol. After 8–13 days the solution was removed and water (about 15%) was added to complete the separation of the dichloromethane layer from methanol/water. The dichloromethane layer was evaporated "in vacuum" (the first dichloromethane extraction) and yielded dark brown solid (1504.1 g; PS $ED_{50}$ 4.6 µg/ml). The recovered dichloromethane was remixed with the upper methanol/water layer, methanol was added to reform a single phase and the mixture was returned to the sponge containers. After 7 days the solvent was again drained, and the solution was mixed with water (15%). The separated dichloromethane layer (second R dichloromethane extraction) yielded 747.3 g (PS $ED_{50}$ 27.0 µg/ml).

The 472.0 g of dichloromethane fraction from the shipping solution was partitioned three times between hexane and 9:1 methanol/water. The hexane layer was discarded. The methanol/water phase was diluted to 3:2 (addition of water) and extracted four times with dichloromethane. The dichloromethane extract was concentrated and the residue (66.31 g) showed significant PS cytotoxic activity (PS $ED_{50}$ 0.16 µg/ml).

The first and second dichloromethane extracts were separately partitioned in a similar manner to the dichloromethane fraction of the shipping solution.

Initially, a chromatographic procedure employing SEPHADEXLH-LH-20 was utilized. The PS active dichloromethane fraction (66.31 g) was first separated on a SEPHADEX LH-20 column (3 Kg; 15×150 cm) with dichloromethane-methanol (3:2) as the eluent. The five eluted fractions were concentrated and tested. The fraction which showed the strongest activity (11.42 g; PS $ED_{50}$ 0.03 µg/ml) was again separated using a SEPHADEX LH-20 column (1.6 kg; 8×110 cm) with hexane-toluene-methanol (3:1:1) which resulted in significant increase in activity (1050 mg; PS $ED_{50}$ 0.005 µg/ml). This fraction still contained an inactive black solid that was removed utilizing a medium pressure (to 50 psi) liquid chromatography column using SILICA GEL 60 (40–63 µm) and elution with solvent gradient: hexane-dichloromethane-methanol→dichloromethane-methanol (6:9:1→1:3). The most active fraction (155 mg; PS $ED_{50}$<0.001 µg/ml) contained a small amount of yellow pigment that was removed on a HPLC reverse phase column (PREPEX 5-20 u, C8) with methanol-water (1:1) as the eluent. The resulting fraction (23.13 mg; PS $ED_{50}$ <0.001 µg/ml) contained the mixture of highly PS active components and was combined with an analogous fraction (8.6 mg; PS $ED_{50}$<0.001 µg/ml) obtained by PS guided separation of the first and second dichloromethane extract. Combined fractions were separated on the same reverse phase HPLC column with methanol-acetonitrile-water (5:5:6). The resulting fraction (10.4 mg; PS $ED_{50}$ $10^{-4}$–$10^{-5}$ µg/ml) contained two major components which were finally purified and separated by HPLC using the mixture of methanol-acetonitrile-water (5:5:8) to afford 4.34 mg of (PS $ED_{50}$ $10^{-4}$–$10^{-5}$ µg/ml) a compound designated as spongistatin 2 and 2.69 mg of a second compound (PS $ED_{50}$ $10^{-4}$–$10^{-5}$ µg/ml) designated as spongistatin 3.

The separation steps are as shown outlined in the Separation Scheme, Parts 1–4 appearing below.

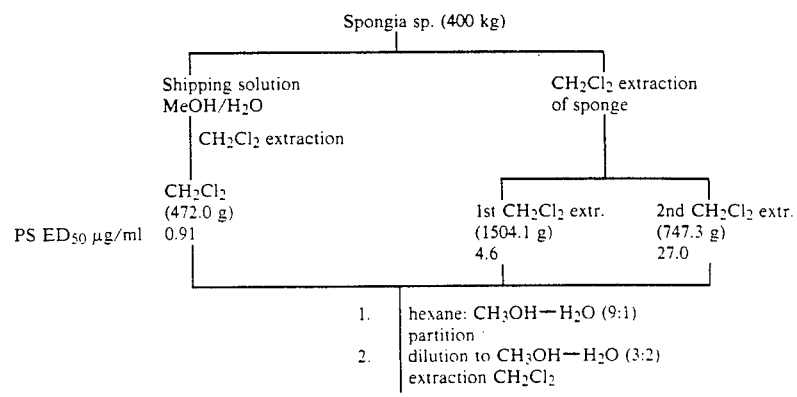

Separation Scheme

Part 1

-continued
Separation Scheme
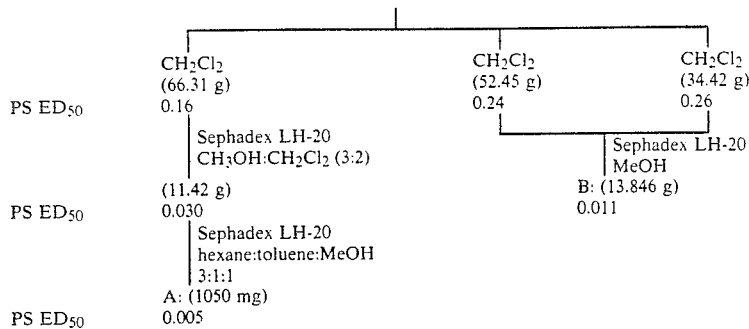
Part 2
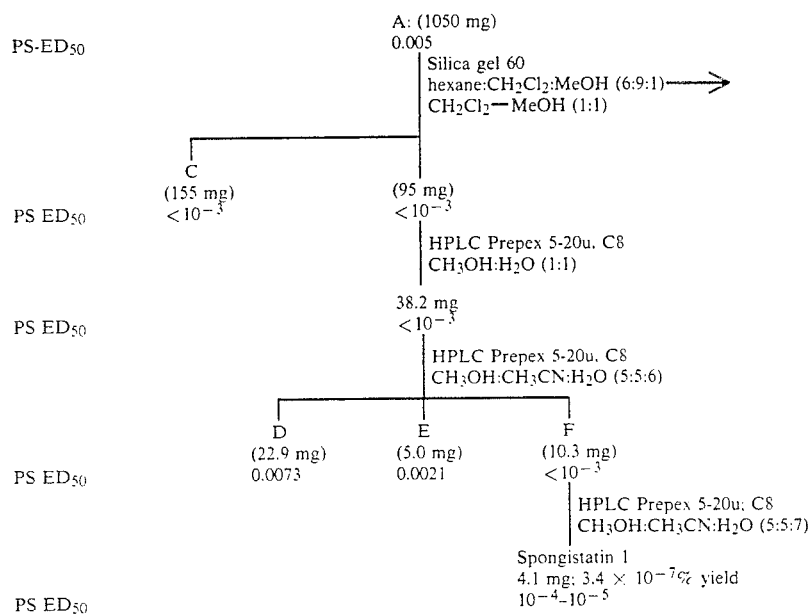
Part 3
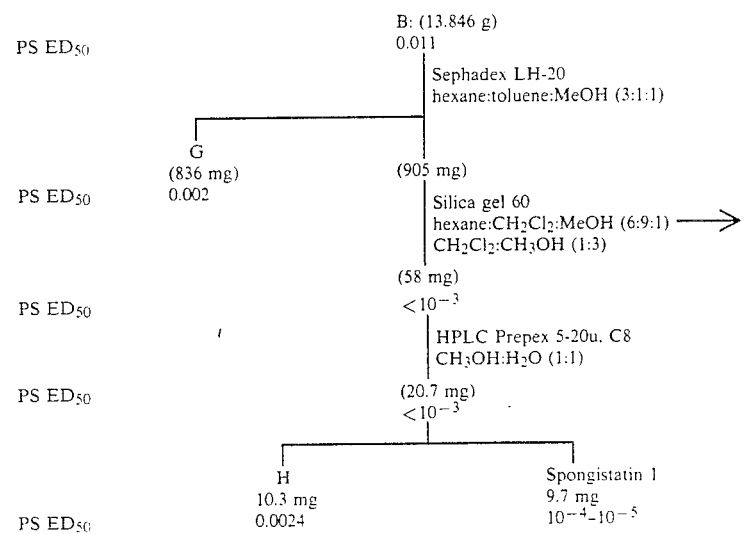
Part 4

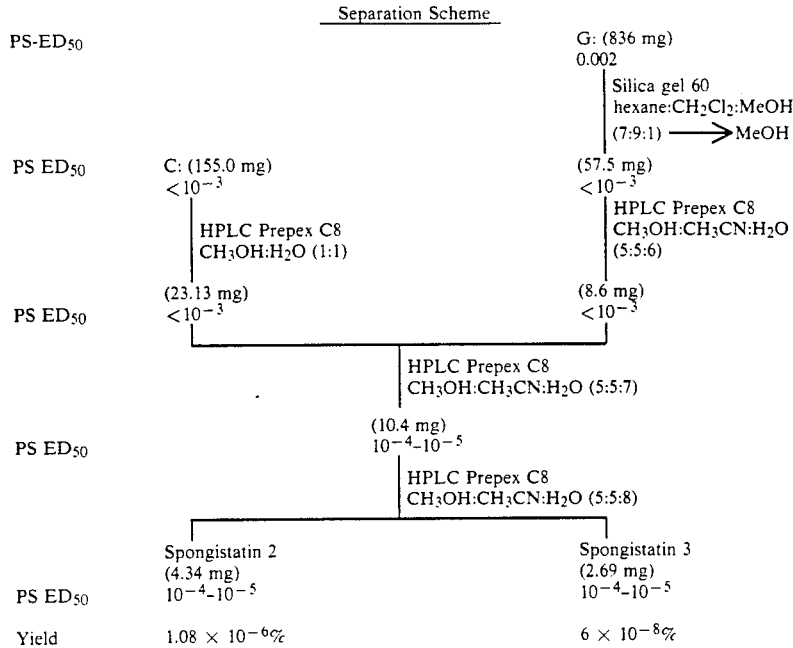

Isolation of Spongistatin 4 and Spongistatin 6

In July, 1980, a large scale recollection (2.409 kg) of *Spirastrella spinispirulifera* preserved in ethanol was completed. The initial extraction, solvent partitioning and preparative HPLC was done on a pilot plant scale. Separation Scheme Part 5 outlines the process whereby sponge material was extracted with 2-propanol, the resulting extract was concentrated, then diluted with water and extracted with methylene chloride. The dried methylene chloride extract (13.86 kg) was next partitioned with hexane and methanol-water (9:1) and the aqueous methanol then taken to dryness (2 kg). The final pilot plant scale high performance liquid chromatography (HPLC) separation (SILICA GEL, $0.15 \times 3$ m column at 150 psi) was carried out using the following step-wise gradient system: methylene chloride-methanol, 100-0 (160 1), 96-4 (205 1) 94-6 (102 1), 93-7 (102 1), 90-10 (102 1), 85-15 (102 1) and 80-20 (110 1). The effluent was collected in 19 liter containers, examined by tlc and like fractions combined and concentrated. The resulting series of active fractions A-F (P388 $ED_{50}$ 0.2 to <0.01 μg/ml) were next subjected to chromatography on SEPHADEX LH-20 in methanol ($10 \times 130$ cm columns) which gave new active fractions G-J (P388 $ED_{50}$ 0.02 to $<10^{-2}$ μg/ml). Fraction G (1.4 g) was applied to the first of three MERCK LOBAR size B SILICA GEL columns ($25 \times 310$ mm) connected in series. A gradient of acetone-hexane (3:47) to acetone-hexane (2:3) was followed by a gradient of methylene chloride-methanol (93:7) to methanol to give active fractions K-O (P388 $ED_{50}$ $1.8 \times 10^{-5}$ to $<10^{-5}$ μg/ml), as shown in Separation Scheme Part 6. Fraction K (38.9 mg) was then applied to two ANALTECH analytical tlc plates, $10 \times 20$ cm. Elution with acetone-hexane (1:1) provided a fraction enriched in a single component, K860 (3.6 mg). A second tlc separation was done, using 3.6 mg on an ANALTECH analytical plate ($7.5 \times 10$ cm) with acetone-hexane, 3:2. A 0.3 mg amount of K860 resulted. From the earlier active fractions H, additional nearly pure K860 was isolated, 6.3 mg, which was combined with the 0.3 mg to give 6.6 mg total.

Further purification using HPLC (ALTEX Programmable Model 420 system, 2 model 110A pumps) with solvent gradient of $CH_2Cl_2$ to 93:7 $CH_2Cl_2$—MeOH on a PARTISIL M9 SILICA GEL column gave 6.3 mg of nearly pure K860. The sample was next chromatographed using HPLC (PARTISIL M9 10/50 ODS-2 column) with a methanol-$H_2O$ (1:1) to methanol gradient to give pure K860, spongistatin 4 (1.4 mg).

Active fraction I (Separation Scheme Part 7) was separated on SILICA GEL RP-2 ($3.7 \times 44$ cm column) using the gradients, water to methanol, methanol to methylene chloride, to give active fraction P (1.75 g). Using the solvent system hexane-toluene-methanol (3:1:1) on SEPHADEX LH-20 ($5.5 \times 96$ cm column) provided active fractions Q through U. Subjecting fraction U (0.173 g) to repetitive separations with a GILSON preparative system (Models 303 and 305 pump and PREPEX C8, $10 \times 250$ mm column) with the isocratic solvent, 36% acetonitrile in water and 1.2–1.8 mg/injection, gave 42.1 mg of mixture containing spongistatin 4. Final separation was achieved by repetitive analytical (GILSON) HPLC separations on LICHROSPHER 100 RP18 ($4.6 \times 250$ mm), 45% acetonitrile in water and 0.2–0.3 mg per injection. The detection of HPLC peaks was by UV, $\lambda = 230$ mm.

In a similar fashion spongistatin 6 was isolated. The final separation by HPLC (Merck LICHROSPHER 100RP18) with 45% acetonitrile in water led to isolation of colorless spongistatin 6 (8.4 mg).

The total amount of spongistatin 4 isolated was 10.7 mg ($4.4 \times 10^{-7}$%, PS $ED_{50}$ $4.9 \times 10^{-5}$ μg/ml); mp 153°–154° C.; $[\alpha]^{22D} = +23.0°$ (c=0.19, $CH_3OH$); UV ($CH_3OH$) $\lambda_{max}$ 229 nm, ε170790 IR (film) 3435, 2938, 1736, 1643, 1593, 1385, 1258, 1177, 1086, 993 cm$^{-1}$; high resolution FABMS, m/z 1219.5546 [M+K]$^+$ corresponding to $C_{61}H_{93}ClO_{20}K$ (calcd mass 1219.5586).

The total amount of spongistatin 6 isolated was 8.4 mg ($3.5 \times 10^{-7}$% yield): P388 $ED_{50}$ $3.4 \times 10^{-3}$ μg/ml; mp 139°–140° C.; $[\alpha]_{D22} + 22.0$ (c, 0.16, $CH_3OH$); UV ($CH_3OH$) $\lambda_{max}$ 223 nm (log $\epsilon$4.27); IR (film) 3431, 2938, 1736, 1645, 1603, 1387, 1256, 1175, 1086, 993 cm$^{-1}$; HRFAB MS m/z 1185.5926 [M+K]$^+$, calcd for $C_{61}H_{94}O_{20}K$ 1185.5922.

SCHEME COMPILATION.
Preparative HPLC of Spirastrella spinispirulifera Extract

| Column | Fractions* | | Amount Concentrate (g) | P388 ED$_{50}$ ($\mu$g/ml) |
|---|---|---|---|---|
| One: 2.0 Kg initial weight | | | | |
| | 1–4 | | 1700 rechromatographed on 2nd column | — |
| | 5–15 | | 0.0 | — |
| | 16–17 | | 12.5 | 17.0 |
| | 18–19 | | 9.0 | 2.3 |
| | 20–21 | A | 16.0 | 0.2 |
| | 22–27 | B | 28.0 | 0.13 |
| | 28–35 | | 11.0 | 1.5 |
| | 36–47 | | 45.0 | 1.4 |
| | 48–51 | | 28.0 | 10.0 |
| Two: 1.7 Kg initial weight | | | | |
| | precipitate, batyl alcohol | | 145.0 | — |
| | 1–2 | | 0.0 | — |
| | 3–9 | | 470.0 | 17.0 |
| | 10–11 | | 150.0 | 1.2 |
| | 12–14 | | 140.0 | 11.0 |
| | 15–18 | | 275.0 | 0.14 |
| | 19–26 | D | 100.0 | <0.01 |
| | 27–34 | E | 35.0 | 0.21 |
| | 35–46+ | F | 175.0 | 0.30 |

Visualization took place with both uv and spray reagents of 5% ceric sulfate in 15% sulfuric acid and 1:2:97 anisaldehyde-sulfuric acid-acetic acid.
*Fraction volume was 19 liter each, and like fractions were combined and concentrated by tlc comparisons. Tlc system was 95:5 methylene chloride-methanol on Brinkman Sil G/UV 254 20 × 20 cm plates with batyl alcohol used as a reference sample.

Separation Scheme Part 5

*Spirastrella spinispirulifera*
2,409 Kg wet weight 1. 2-propanol
2. concentrate extrate
3. water
4. extract with $CH_2Cl_2$, 4x $CH_2Cl_2$ (13.86 Kg)

1. hexane
2. MeOH—$H_2O$ (9:1), 4x hexane (9.3 Kg)

MeOH—$H_2O$ (2 Kg)

Preparative HPLC, 2× silica gel (29 Kg/ column), $CH_2Cl_2$—MeOH gradient

| Active Fractions | A | B | C | D | E | F |
|---|---|---|---|---|---|---|
| Weight (g) | 16 | 28 | 275 | 100 | 35 | 175 |
| P388-ED$_{50}$ ($\mu$g/ml) | 0.20 | 0.13 | 0.14 | 0.011 | 0.21 | 0.30 |
| —T/C (mg/Kg) | — | — | 178 (30) | 169 (1.8) | 232 (37.5) | 154 (29.5) |

Sephadex LH-20, MeOH (10 × 130 cm)

| Active Fractions | G | H | I | J |
|---|---|---|---|---|
| Weight (g) | 1.4 | 5.4 | 29.1 | 36.0 |
| P388 ED$_{50}$ ($\mu$g/ml) | <10$^{-2}$ | <10$^{-2}$ | <10$^{-2}$ | 2.2 × 10$^{-2}$ |

Separation Scheme Part 6

Fraction G (1.4 g)

silica gel
1. acetone-hexane gradient
2. $CH_2Cl_2$—MeOH gradient

| Active Fractions | K | L | M | N | O |
|---|---|---|---|---|---|
| Weight (mg) | 38.9 | 13.5 | 7.3 | 14.0 | 20.7 |
| P388 ED$_{50}$ ($\mu$g/ml) | 1.8 × 10$^{-5}$ | — | <10$^{-5}$ | — | <10$^{-5}$ | silica gel
analytical prep tlc. 10 × 20 cm
1:1 acetone:hexane

-continued

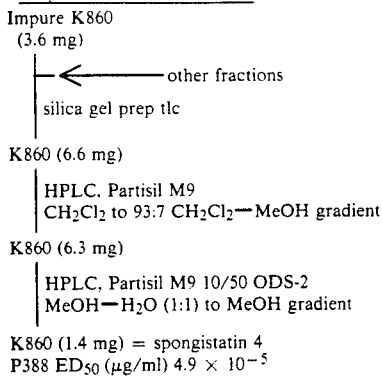

Separation Scheme Part 6

Impure K860 (3.6 mg)
— ← other fractions
| silica gel prep tlc
K860 (6.6 mg)
| HPLC, Partisil M9
| $CH_2Cl_2$ to 93:7 $CH_2Cl_2$—MeOH gradient
K860 (6.3 mg)
| HPLC, Partisil M9 10/50 ODS-2
| MeOH—$H_2O$ (1:1) to MeOH gradient
K860 (1.4 mg) = spongistatin 4
P388 $ED_{50}$ (μg/ml) $4.9 \times 10^{-5}$

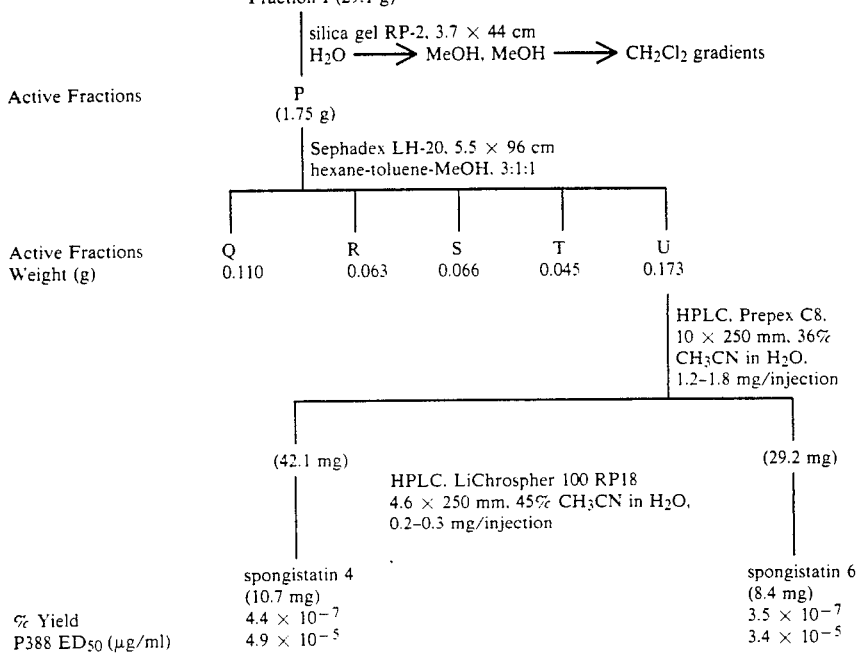

Separation Scheme Part 7

Fraction I (29.1 g)
| silica gel RP-2, 3.7 × 44 cm
| $H_2O \longrightarrow$ MeOH, MeOH $\longrightarrow CH_2Cl_2$ gradients Active Fractions    P (1.75 g)
| Sephadex LH-20, 5.5 × 96 cm
| hexane-toluene-MeOH, 3:1:1

Active Fractions    Q      R      S      T      U
Weight (g)        0.110  0.063  0.066  0.045  0.173

HPLC, Prepex C8, 10 × 250 mm, 36% $CH_3CN$ in $H_2O$. 1.2–1.8 mg/injection (42.1 mg)                              (29.2 mg)
| HPLC, LiChrospher 100 RP18
| 4.6 × 250 mm, 45% $CH_3CN$ in $H_2O$,
| 0.2–0.3 mg/injection spongistatin 4           spongistatin 6
(10.7 mg)                (8.4 mg)
% Yield          $4.4 \times 10^{-7}$           $3.5 \times 10^{-7}$
P388 $ED_{50}$ (μg/ml)  $4.9 \times 10^{-5}$           $3.4 \times 10^{-5}$ The complex structural determination of spongistatin 1 was accomplished using primarily high field (400 and 500 MHz) 2D-NMR with extensive connectivity (HMBC, NOE) experiments. Once the general relationship of spongistatin 1 to spongistatin 2 and 3 was revealed, the structure solutions were markedly accelerated. The data and spectral interpretation relied upon in arriving at the spongistatin 1 structure were utilized as follows. The $^{13}C$ NMR spectra of spongistatin 2 in $CD_3OD$ indicated sixty-three carbon signals, while the $^1H$ NMR spectra exhibited four methyl doublet signals at δ1.04, 1.21, 0.91, 0.84, one methyl singlet at δ1.14, two acetyl methyl singlets at δ1.86 and 2.01 and one methoxyl singlet at δ3.33. The presence of three ester carbonyl groups was evident from the $^{13}C$ NMR signals at δ173.54, 171.23 and 172.79 and the $^1H$ NMR signals at δ2.64 (broad doublet, J = 18 Hz), and 2.57 (doublet of doublets, J = 10, 18 Hz). The presence of a ketone carbonyl and its connection were also suggested by the signals at δ2.92 (doublet of doublets, J = 10, 18 Hz), 2.74 (broad doublet, J = 18 Hz), 1.21 (3H, doublet, J = 7.0 Hz), and the $^{13}C$ NMR signals at δ 213.27, 51.41, and 14.26. Five double bonds were obvious from the $^1H$ NMR signals at δ4.92 (broad singlet), 4.85 (broad singlet), 5.40 (triplet, J = 10 Hz) , 5.47 (multiplet) , 4.95 (broad singlet), 4.93 (broad singlet), 5.71 (doublet of doublets, J = 7, 15 Hz), 6.23 (broad doublet of doublets (J = 10, 15 Hz), 6.34 (doublet of doublets of doublets, J = 10, 10, 16 Hz), 5.18 (broad doublet, J = 16 Hz), 5.05 (broad doublet, J = 10 Hz) and the $^{13}C$ NMR signals at δ148.71, 114.86, 131.49, 134.25, 143.99, 116.17, 137.66, 132.06, 138.02, 117.52. Three hemiacetal or ketal signals appeared at δ99.59, 100.31, and 99.32.

The preceding NMR data suggested that spongistatin 2 had a structure similar to that of spongistatin 1. Detailed analysis of 2D COSY, $^1H$—$^{13}C$ correlation and HMBC spectra completed the assignment of the proton and the carbon-13 signals. Indeed, direct comparison of the NMR data from spongistatin 1 and spongistatin 2 suggested that the difference between the two compounds was at C-50. The presence of an ABX spin system in the $^1H$ NMR spectra of spongistatin 2 at δ5.05 (broaden doublet, J = 10 Hz), 5.18 (broaden doublet, J=16 Hz) and 6.34 (doublet of doublets of doublets, J=10, 10, 16 Hz) verified this assumption. Also in accord with this structural difference was the observation that signals for C-51, C-50, C-49, C-48, C-47 in spongistatin 2 were shifted Δδ 1.32, −1.59, 4.17, −1.22, and 0.63 ppm compared to the relevant chemical shifts in spongistatin 1. Other signals were essentially the same as those of spongistatin 1. Thus, it became clear that hydrogen was attached to C-50 in spongistatin 2 rather than a chlorine atom as in spongistatin 1. Extensive HMBC studies of spongistatin 2 in $CD_3OD$ and $CD_3CN$ supported this conclusion.

The $^{13}C$ NMR spectra of spongistatin 3 pointed to sixty-one carbon atoms that included two ester carbonyl signals at δ174.00, 171.19 and a ketone carbonyl at δ213.11. Three hemiacetal or ketal signals were found at δ101.64, 100.29 and 99.22. Seven methyl signals appeared at δ11.93, 14.25, 11.83, 12.85, 30.10, 20.67, and 55.92. One of these corresponded to an acetyl group and one to a methoxyl group. Ten $SP^2$ signals arose at δ150.29, 114.27, 131.47, 134.34, 143.85, 116.33, 138.83, 127.93, 139.64 and 116.25. In the $^1H$ NMR spectra of spongistatin 3, the six methyl signals were assigned to δ1.15 (singlet), 1.85 (singlet), 1.03 (doublet, J=6.7 Hz), 1.21 (doublet, J=7.1 Hz), 0.91 (doublet, J=7.2 Hz), 0.84 (doublet, J=6.7 Hz), the methoxyl singlet to δ3.33. All were in accord with seven signals viewed in the $^{13}C$ NMR spectrum. These interpretations suggested that the structures of spongistatin 3 and spongistatin 1 were closely related except that spongistatin 3 contained one less acetyl group.

Direct comparison of spongistatin 1 and 3 showed that the $^{13}C$- and the $^1H$-NMR signals in the C-47 to C-51 region were very similar and suggested (and confirmed by MS) the presence of a chlorine atom in spongistatin 3. Analysis of the 2D COSY spectra presented by spongistatin 3 allowed assignment of the $^{13}C$ and the $^1H$ NMR signals. The diamagnetic shift (while the coupling pattern remained the same) of the H-5 signal from δ5.03 in spongistatin 1 to δ4.01 in spongistatin 3 established the hydroxyl group at C-5 and assignment of structure 3 to spongistatin 3.

Once the structure of spongistatin 1 was established and its relationship to spongistatin 4 revealed, the structure solution for this Spirastrella antineoplastic constituent was accelerated. The $^1H$-NMR spectrum of spongistatin 4, one acetate, one methoxy, and another five methyl groups were obvious by the signals at δ2.03 (3H, singlet), 3.33 (3H, singlet), 1.13 (3H, singlet), 0.97 (3H, doublet, J=6.9 Hz), 1.12 (3H, doublet, J=7.3 Hz), 0.91 (3H, doublet, J=7.2 Hz) and 0.83 (3H, doublet, J=6.6 Hz). The chemical shift of the acetyl methyl singlet was indicative of its attachment at the C-5 position rather than at C-15 as in the case of spongistatin 3. Detailed analysis of the 2D COSY spectrum of spongistatin 4 and the difference in the chemical shifts of H-5 and H-15 readily confirmed a C-5 acetyl group. Both the $^{13}C$-and $^1H$-NMR signals from C-44 to C-51 were basically the same as those of spongistatins 1 and 3 and was in agreement with the presence of a chlorine atom (supported by the HRFABMS) at C-50. The NMR signals arising from the remaining structure were essentially the same as those of spongistatin 3. Thus, structure 4 was assigned to spongistatin 4.

The structures assigned spongistatins 1–4 required extensive high field (400 and 500 MHz) 2-D NMR and high resolution mass spectral interpretations that were quite difficult. But, results of those challenging analyses proved very important to completing the structural elucidation of spongistatin 6. The high resolution FAB mass spectrum of spongistatin 6 allowed assignment of molecular formula $C_{61}H_{94}O_{20}$ by peak matching at m/z 1185.5 $[M+K]^+$. The $^1H$-NMR spectrum of spongistatin 6 indicated a spongistatin-type ring system. For example, the four methyl signals present in spongistatins 1–4 were found at δ0.97 (d, J=6.8 Hz), 1.12 (d, J =7.1 Hz), 0.91 (d, J=7.1 Hz), and 0.83 (d, J=6.6 Hz). The $^1H$ signals at δ2.90 (broad d, J=18 Hz), 2.83 and a $^{13}C$ signal at δ 15.29 were characteristic of the spongipyran C-17 carbonyl system. The presence of an ABX spin system at δ5.04 (broad d, J=11 Hz), 5.17 (broad d, J=17 Hz), 6.33 (d,d,d, J=11, 11, 17 Hz) suggested a proton rather than a chlorine atom at C-50 similar to that of spongistatin 2. The presence of one acetyl group was evident by $^1H$ and $^{13}C$ signals at δ2.03 (s, 3H) 172.80, and 21.65. The $^1H$—$^1H$ COSY and $^1H$—$^{13}C$ COSY experiments established the $^1H$ and $^{13}C$ assignments. The chemical shifts of the H-5 and H-15 signals at δ5.03 (1H, broad s) and 3.83 (1H, broad d, J=9 Hz) readily pointed to attachment of the acetyl group at C-5. These $^1H$— and $^{13}C$—NMR interpretations combined with results of the HMBC assignments led to structure 5 for spongistatin 6.

The NMR assignments for spongistatin 1, spongistatin 2, spongistatin 3, spongistatin 4 and spongistatin 6 are shown in Tables I, II, III, IV and V below.

Evaluation of spongistatins 1–4, and 6 against the U.S. National Cancer Institute panel of 60 human cancer cell lines gave dramatic results. Comparative testing of spongistatins 1, 2, 3, 4 and 6 in the NCI 60 cell line in vitro screening panel revealed an overall potency of spongistatins 2, 3, 4 and 6 comparable to spongistatin 1 (e.g., panel mean $GI_{50}$ $10^{-10}M$; Table IX). These compounds are among the most potent of all substances tested to date in the NCI screen. Interestingly, several of the human breast cancer cell lines recently incorporated into the NCI screening panel were among the most sensitive (e.g., $GI_{50}$ $10^{-11}$–$10^{-12}M$). The structural variations thus far observed in this intriguing new family of antineoplastic substances do not result in substantial loss of the critical in vitro activity attributes. The advantageous or disadvantageous effects of these structrual variations upon the in vivo activity potential is unknown, but will be addressed in further biological evaluations of all of the available compounds so remarkably active in vitro.

TABLE I

NMR assignments for spongistatin 1 recorded in $CD_3CN$. Coupling constants are in Hz (in parenthesis). The mixing time for the HMBC was set at 130 microsecond).

| | $^{13}C$(100 MHz) | XHCorr. (400 MHz) | HMBC (500 MHz, C to H) |
|---|---|---|---|
| 1 | 173.07 | | H-2; H-41 |
| 2 | 40.86 | 2.44 dd(10, 18) 2.53 dd(2, 18) | H-4 |
| 3 | 63.59 | 4.25 brt(10) | H-2; H-8 |
| 4 | 34.65 | 1.55*; 1.68* | H-2; H-6 |
| 5 | 67.06 | 4.92 brs | |
| 6 | 38.17 | 1.67 dd(5, 14); 1.78 brd(14) | H-5; H-8 |
| 7 | 99.26 | | H-6; H-8; H-9a |
| 8 | 46.76 | 1.47 d(14); 1.60* | H-9a; H-6 |
| 9 | 69.64 | | H-9a; OH(C9); H-8 |
| 9a | 30.21 | 1.06 s | H-8; H-10 |
| 10 | 44.96 | 1.28*; 1.55* | H-9a; H-12; H-8 |
| 11 | 65.00 | 4.25 brt(10) | H-12; H-13a; H-15; H-6 |
| 12 | 44.24 | 1.99*; 2.27 brd(14) | H-10; H-13a |
| 13 | 148.03 | | H-12; H-13a; H-14a; H-15 |
| 13a | 114.86 | 4.83 brs; 4.83 brs | H-12; H-14 |

TABLE I-continued

NMR assignments for spongistatin 1 recorded in CD₃CN. Coupling constants are in Hz (in parenthesis). The mixing time for the HMBC was set at 130 microsecond).

| ¹³C(100 MHz) | XHCorr. (400 MHz) | HMBC (500 MHz. C to H) |
|---|---|---|
| 14 | 36.60 | 2.78* | H-13a; H-14a; H-15; H-16; H-12 |
| 14a | 12.09 | 1.04 d(6.9) | H-15 |
| 15 | 75.34 | 5.12 dd(1.7, 11) | H-13a; H-14a; H-16; H-16a |
| 16 | 47.62 | 3.04 dq(7, 11) | H-15; H-16a |
| 16a | 13.73 | 1.15 d(7) | H-15; H-16 |
| 17 | 213.52 | | H-16; H-16a; H-18; H-15 |
| 18 | 51.94 | 2.62 brd(18) 2.86 dd(11, 18) | H-16; H-20 |
| 19 | 66.16 | 4.00 brt(11) | H-18 |
| 20 | 37.70 | 0.97 ddd(12, 12, 12); 1.98* | H-18; H-22 |
| 21 | 73.98 | 3.46 tt(4, 4, 12, 12) | H-22; H-OMe; H-20 |
| 22 | 44.18 | 1.08 t(12); 1.99* | H-21; H-20 |
| 23 | 99.91 | | H-18; H-22; H-24; H-27 |
| 24 | 34.91 | 1.55*; 2.28* | H-22 |
| 25 | 64.41 | 3.93 brm | H-26; H-27; H-24 |
| 26 | 39.11 | 1.57*; 1.57* | H-28; H-24 |
| 27 | 61.22 | 5.00 ddd(4.3, 10, 10) | H-26; H-29 |
| 28 | 131.22 | 5.32 brt(10) | H-27; H-30 |
| 29 | 133.42 | 5.48 ddd(10, 10, 10) | H-27; H-30 |
| 30 | 28.07 | 2.00*; 2.19* | H-28; H-29; H-31; H-32 |
| 31 | 27.04 | 1.23*; 1.60* | H-29; H-33; H-30; H-32 |
| 32 | 32.82 | 1.30 m; 1.42 m | H-33 |
| 33 | 67.15 | 4.13 dt(3.4, 3.4, 8) | H-34a |
| 34 | 39.32 | 1.57 m | H-34a; H-36 |
| 34a | 11.55 | 0.81 d(7) | H-33; H-34 |
| 35 | 71.47 | 3.65 brs | H-34a; H-33; H-36 |
| 36 | 33.79 | 1.61*; 1.89* | OH(C37); H-34 |
| 37 | 99.41 | | H-33; H-36; OH(C37); H-38 |
| 38 | 73.11 | 3.34 brs | H-36 |
| 39 | 81.30 | 3.72 brd(10) | H-40a; H-41 |
| 40 | 37.26 | 1.91* | H-40a; H-39; H-41 |
| 40a | 12.69 | 0.74 d(7) | H-40; H-41 |
| 41 | 80.60 | 4.75 dd(9, 11) | H-40a; H-39; H-40; H-42; H-43 |
| 42 | 43.11 | 3.12 t(9) | H-40; H-41; H-43; H-40a |
| 43 | 78.72 | 3.39 brt(9) | H-39; H-41; H-42; H-44 |
| 44 | 40.24 | 2.08*; 2.76 brd(13) | H-42; H-46; H-45a |
| 45 | 144.00 | | H-45a; H-43; H-44; H-46; H-47 |
| 45a | 116.61 | 4.86 brs; 4.89 brs | H-44; H-46 |
| 46 | 43.93 | 2.33 brdd(7, 14); 2.19* | H-44; H-45a |
| 47 | 70.13 | 4.36 ddd(6, 7, 11) | H-46; H-48 |
| 48 | 139.21 | 6.11 dd(6, 15) | H-46; H-47 |
| 49 | 126.99 | 6.41 brd(15) | H-47; H-48; H-51 |
| 50 | 139.21 | | H-48; H-49; H-51 |
| 51 | 116.48 | 5.35 brs; 5.45 brs | H-48; H-49 |
| OMe | 55.72 | 3.24 s | H-21 |
| OAc | 21.78 171.61 | 1.94 s | H-OAc(δ1.94); H-5 |
| OAc | 21.00 170.21 | 1.84 s | H-OAc(δ1.84); H-15 |
| OH(C25) | | 4.39 d(9.9) | |
| OH(C37) | | 4.73 d(2) | |
| OH(C9) | | 4.32 brs | |
| OH | | 3.83 brm | |

*Coupling constants for these signals were not measured due to overlapping.

TABLE II

NMR assignments for spongistatin 2 recorded in CD₃CN. Coupling Constants are in Hz (in parenthesis). Some of the Coupling Constants were not Measured due to Overlapping.

| ¹³C (100 MHz) | ¹H (400 MHz) |
|---|---|
| 1 | 172.99p | |
| 2 | 40.79p | 2.53 dd(2, 16); 2.48 dd(10, 16) |
| 3 | 63.53n | 4.26* |
| 4 | 34.57p | 1.55*; 1.69* |
| 5 | 66.98n | 4.94 brs |
| 6 | 38.08p | 1.79*; 1.68* |
| 7 | 99.18p | |
| 8 | 46.67p | 1.48 d(14); 1.61* |
| 9 | 69.56p | |

TABLE II-continued

NMR assignments for spongistatin 2 recorded in CD₃CN. Coupling Constants are in Hz (in parenthesis). Some of the Coupling Constants were not Measured due to Overlapping.

| ¹³C (100 MHz) | ¹H (400 MHz) |
|---|---|
| 9a | 30.12n | 1.07 s |
| 10 | 44.88p | 1.55*; 1.28* |
| 11 | 64.61n | 4.26* |
| 12 | 44.11p** | 2.28*; 2.02* |
| 13 | 147.95p | |
| 13a | 114.79p | 4.85 brs; 4.85 brs |
| 14 | 36.51n | 2.79* |
| 14a | 12.02n | 1.06 d(7) |
| 15 | 75.26n | 5.12 dd(2, 10) |
| 16 | 47.52n | 3.06 brdq(7.2, 10) |
| 16a | 13.63n | 1.17 d(6.8) |
| 17 | 213.38p | |
| 18 | 51.86p | 2.87 dd(10, 18); 2.63 brd(18) |
| 19 | 66.06n | 4.01 brt(11) |
| 20 | 37.62p | 0.98 ddd(11, 12, 12) |
| 21 | 73.90n | 3.48 brm |
| 22 | 43.92p** | 1.99*; 1.08* |
| 23 | 98.82p | |
| 24 | 34.82p | 2.29 brd(12); 1.55* |
| 25 | 64.31n | 3.95 brm |
| 26 | 38.99p | 1.55*; 1.55* |
| 27 | 61.13n | 5.02 ddd(4, 10, 10) |
| 28 | 131.14n | 5.34 brt(10) |
| 29 | 133.36n | 5.50 brddd(7, 8, 10) |
| 30 | 27.98p | 2.21*; 2.02* |
| 31 | 26.93p | 1.62*; 1.28* |
| 32 | 32.74p | 1.42*; 1.33* |
| 33 | 67.06n | 4.14 dt(8.4) |
| 34 | 39.23n | 1.60* |
| 34a | 11.47n | 0.83 d(7.2) |
| 35 | 71.40n | 3.68 brs |
| 36 | 33.69p | 1.90*; 1.60* |
| 37 | 99.33p | |
| 38 | 73.02n | 3.36 brd(9) |
| 39 | 81.21n | 3.75 brd(10) |
| 40 | 37.18n | 1.90* |
| 40a | 12.61n | 0.76 d(7.2) |
| 41 | 80.54n | 4.76 dd(8.4, 9) |
| 42 | 73.02n | 3.13 brt(9) |
| 43 | 78.61n | 3.40 brt(9) |
| 44 | 40.08p | 2.77 brd(14); 2.03* |
| 45 | 144.13p | |
| 45a | 116.21p | 4.88 brs; 4.85 brs |
| 46 | 44.17p** | 2.34 brdd(6, 12); 2.15* |
| 47 | 70.68n | 4.26* |
| 48 | 138.28n | 5.72 dd(6, 15) |
| 49 | 130.97n | 6.23 brdd(11, 15) |
| 50 | 137.80n | 6.36 ddd(1 1, 11, 16) |
| 51 | 117.38p | 5.20 dd(2, 16) |
| OMe | 55.64n | 3.26 s |
| OAc | 171.54p | |
| | 21.70p | 1.96 s |
| OAc | 170.11p | |
| | 20.92n | 1.86 s |
| C-9 OH | | 4.34 s |
| C-25 OH | | 4.40* |
| C-35 OH | | 3.85 m |
| C-37 OH | | 4.74 d(2) |
| C-38 OH | | 2.88* |
| C-42 OH | | 4.40* |

*Coupling constants for these signals were not measured due to overlapping.
**NMR signal assignments for C-12, 22 and C-46 may have been interchanged.

TABLE III

NMR assignments for spongistatin 3 recorded in CD₃OD. Coupling Constants are in Hz (in parenthesis).

| ¹³C (100 MHz) | ¹H (400 MHz) |
|---|---|
| 1 | 174.00 | |
| 2 | 40.29 | 2.68; 2.62 |
| 3 | 62.98 | 4.25 brt(10) |
| 4 | 37.86 | 1.60*; 1.60* |
| 5 | 66.14 | 4.01 brs |
| 6 | 39.81 | 1.82 brd(14); 1.70* |
| 7 | 101.64 | |
| 8 | 46.15 | 1.73*; 1.57 d(14) |

TABLE III-continued

NMR assignments for spongistatin 3 recorded in CD₃OD. Coupling Constants are in Hz (in parenthesis).

| | $^{13}$C (100 MHz) | $^{1}$H (400 MHz) |
|---|---|---|
| 9 | 69.76 | |
| 9a | 30.10 | 1.15 s |
| 10 | 45.03 | 1.68*; 1.44 brt(12) |
| 11 | 65.91 | 4.64 brt(11) |
| 12 | 44.30 | 2.47 brd(14);2.15* |
| 13 | 150.29 | |
| 13a | 114.27 | 4.89*; 4.89* |
| 14 | 37.13 | 3.00 brm |
| 14a | 11.93 | 1.03 d(6.7) |
| 15 | 75.04 | 5.38* |
| 16 | 46.08 | 3.10 dq(7, 11) |
| 16a | 14.25 | 1.21 d(7.1) |
| 17 | 213.11 | |
| 18 | 51.22 | 2.92 dd(11, 18); 2.74 brd(18) |
| 19 | 66.56 | 4.09 brt(11) |
| 20 | 37.97 | 2.05*;1.02*; |
| 21 | 74.64 | 3.57 m |
| 22 | 44.32 | 2.05*; 1.20* |
| 23 | 100.29 | |
| 24 | 34.88 | 2.38 brd(14); 1.62* |
| 25 | 65.10 | 4.01 brs |
| 26 | 39.07 | 1.64*; 1.64* |
| 27 | 61.69 | 5.03 m |
| 28 | 131.47 | 5.40* |
| 29 | 134.34 | 5.48 m |
| 30 | 28.26 | 2.15*; 2.15* |
| 31 | 27.70 | 1.74*; 1.28* |
| 32 | 33.38 | 1.45*; 1.28* |
| 33 | 68.00 | 4.20 brd(8) |
| 34 | 40.04 | 1.62* |
| 34a | 11.83 | 0.91 d(7.2) |
| 35 | 72.13 | 3.77 brd(2.7) |
| 36 | 34.17 | 2.02*; 1.66* |
| 37 | 99.22 | |
| 38 | 73.45 | 3.41 brs |
| 39 | 81.83 | 3.82 brd(10) |
| 40 | 37.69 | 1.98 m |
| 40a | 12.85 | 0.84 d(6.7) |
| 41 | 80.74 | 4.89* |
| 42 | 73.66 | 3.18 t(9) |
| 43 | 79.97 | 3.43 brt(9) |
| 44 | 40.68 | 2.80 brd(14); 2.20* |
| 45 | 143.85 | |
| 45a | 116.33 | 4.98 brs; 4.97 brs |
| 46 | 44.30 | 2.36 dd(6, 14); 2.26 brdd(6, 14) |
| 47 | 71.10 | 4.38 ddd(6, 6, 6) |
| 48 | 138.83 | 6.15 dd(6, 15) |
| 49 | 127.93 | 6.42 brd(15) |
| 50 | 139.64 | |
| 51 | 116.25 | 5.44 brs;5.35 brs |
| OMe | 55.90 | 3.33 s |
| OAc | 171.19 | |
| | 20.67 | 1.85 s |

*Coupling constants for these signals were not measured due to overlapping.

TABLE IV

NMR assignments for Spongistatin 4 in CD₃OD (n and p are APT results, coupling constants are in Hz in parenthesis).

| | $^{13}$C (100 MHz) | $^{1}$H (400 MHz) | HMBC (500 MHz, C to H) |
|---|---|---|---|
| 1 | 173.42p | | H-41, H-2, H-3 |
| 2 | 39.98p | 2.65*; 2.60* | |
| 32 | 62.73n | 4.39* | H-2 |
| 4 | 34.86p | 1.74*; 1.60* | H-6 |
| 5 | 67.85n | 5.02 brs | H-6 |
| 6 | 38.37n | 1.93 brd(14); 1.72* | H-5, H-8 |
| 7 | 99.59p | | H-5, H-6 |
| 8 | 46.86p | 1.69*; 1.49 d(14) | H-9a, H-6, H-10 |
| 9 | 70.26p | | H-9a |
| 9a | 30.02n | 1.13 s | H-8 |
| 10 | 45.42p | 1.55 brd(12); 1.35 t(12) | H-8, H-9a |
| 11 | 64.96n | 4.67 brt(11) | |
| 12 | 44.45p | 2.27*; 2.23* | H-13a, H-10 |
| 13 | 148.46p | | H-14a, H-13a, H-12, H-14, H-15 |
| 13a | 114.91p | 5.04 brs; 4.92 brs | H-12, H-14 |
| 14 | 37.56n | 2.82* | H-13a, H-14a, H-12, H-15 |
| 14a | 11.30n | 0.97 d(6.9) | H-15 |
| 15 | 73.75n | 3.82 brd(9) | H-16a, H-14a |
| 16 | 49.99n | 2.82* | H-16a, H-15 |
| 16a | 14.25n | 1.12 d(7.3) | H-15 |
| 17 | 215.29p | | H-15, H-16a, H-18 |
| 18 | 52.34p | 2.89*; 2.80* | H-20 |
| 19 | 66.67n | 4.11 brdd(10, 12) | H-18, H-20 |
| 20 | 38.01p | 2.05*; 1.02 ddd(12, 12, 12) | H-22 |
| 21 | 74.65n | 3.58 m | H-OMe, H-20, H-22 |
| 22 | 44.13p | 2.05*; 1.21 t(12) | |
| 23 | 100.18p | | H-25, H-24, H-22 |
| 24 | 34.86p | 2.41 brd(14); 1.63* | H-22 |
| 25 | 65.22n | 4.04 brs | H-24 |
| 26 | 39.16p | 1.64*; 1.64* | H-24, H-28 |
| 27 | 61.74p | 5.03 t(4, 9, 11) | H-25, H-28, H-29 |
| 28 | 131.43n | 5.41 brt(11) | H-27 |
| 29 | 134.08n | 5.48 ddd(5, 9, 11) | H-27 |
| 30 | 28.19p | 2.18*; 2.14* | H-28 |
| 31 | 27.67p | 1.72*; 1.27* | H-33 |
| 32 | 33.29p | 1.44*; 1.28* | H-33 |
| 33 | 67.99n | 4.20 brd(8) | H-34a, H-35 |
| 34 | 39.98n | 1.62* | H-34a, H-36 |
| 34a | 11.92n | 0.91 d(7.2) | H-33 |
| 35 | 72.07n | 3.77 brd(3) | H-34a, H-36 |
| 36 | 34.18p | 2.01*; 1.66* | H-38 |
| 37 | 99.26p | | H-35, H-38 |
| 38 | 73.38n | 3.40 brs | H-40, H-40a |
| 39 | 81.80n | 3.80 brd(9) | H-38, H-40a |
| 40 | 37.71n | 2.00 m | H-40 |
| 40a | 12.86n | 0.83 d(6.6) | H-39, H-40, H-40a, H-42 |
| 41 | 80.55n | 4.85 t(9) | H-41, H-43, H-44 |
| 42 | 73.75n | 3.16 t(9) | H-44 |
| 43 | 79.89n | 3.41 brt(9) | H-45a, H-46 |
| 44 | 40.68p | 2.80*; 2.18* | H-44, H-46, H-47, H-43, H-44, H-46 |
| 45 | 143.85p | | |
| 45a | 116.33p | 4.97 brs; 4.96 brs | H-44, H-46 |
| 46 | 44.32p | 2.33 dd(7, 14); 2.26 brdd(7, 14) | H-44, H-45a, H-47, H-48 |
| 47 | 71.08n | 4.38* | H-46, H-48, H-49 |
| 48 | 138.80n | 6.14 dd(6, 15) | H-46, H-47 |
| 49 | 127.88n | 6.42 brd(15) | H-47, H-51 |
| 50 | 139.62p | | H-48, H-49, H-51 |
| 51 | 116.18p | 5.43 brs; 5.34 brs | H-49 |
| OMe | 55.87n | 3.33 s | |
| C-5Ac | 172.80p | | H-OAc |
| | 21.63p | 2.03 s | |

*Coupling constants for these signals are not measured due to overlapping.

TABLE V

NMR assignments for Spongistatin 6 in CD₃OD (n and p are APT results, coupling constants are in Hz in parenthesis). The mixing time for the HMBC experiment was set at 130 Micro second.

| | $^{13}$C (100 MHz) | $^{1}$H (400 MHz) | HMBC (500 MHz, C to H) |
|---|---|---|---|
| 1 | 173.44p | | H-41 |
| 2 | 40.01p | 2.66 brd(18; 2.60 dd(10, 18) | |
| 3 | 62.76n | 4.40 brdd(10, 12 | H-2, H-8 |
| 4 | 34.89p | 1.76*; 1.61* | |
| 5 | 67.88n | 5.03 brs | |
| 6 | 38.41n | 1.94 brd(14); 1.72* | H-8 |
| 7 | 99.63p | | H-8 |
| 8 | 46.90p | 1.71*; 1.50 d(14) | H-9a, H-6, |
| 9 | 70.27p | | H-9a, H-8 |
| 9a | 30.06n | 1.13 s | H-8 |
| 10 | 45.42p | 1.55 brd(12); 1.36 brdd(12, 14) | H-8, H-9a |
| 11 | 64.98n | 4.68 brdd(10,12) | H-8 |
| 12 | 44.45p | 2.27*; 2.22* | H-10 |
| 13 | 148.50p | | H-13a, H-14a, H-12, H-15 |
| 13a | 114.93p | 5.04 brs; 4.92 brs | H-12 |

TABLE V-continued

NMR assignments for Spongistatin 6 in CD$_3$OD (n and p are APT results, coupling constants are in Hz in parenthesis). The mixing time for the HMBC experiment was set at 130 Micro second.

| $^{13}$C (100 MHz) | $^1$H (400 MHz) | HMBC (500 MHz, C to H) |
|---|---|---|
| 14  37.61n | 2.82* | H-13a, H-14a, H-12 |
| 14a 11.33n | 0.97 d(6.8) | H-15 |
| 15  73.78n | 3.83 brd(9) | H-16a, H-14a |
| 16  50.03n | 2.80* | H-16a, H-15 |
| 16a 14.27n | 1.12 d(7.1) | H-15, H-16 |
| 17  215.29p |  | H-15, H-16a, H-18 |
| 18  52.37p | 2.90 brd(18); 2.80* | H-20, H-16 |
| 19  66.70n | 4.11 brdd(10, 12) | H-18, |
| 20  38.05p | 2.04*; | H-22, H-18 |
|  | 1.02 ddd(12, 12, 12) |  |
| 21  74.68n | 3.59 m | H-OMe, H-22 |
| 22  44.17p | 2.06*; 1.21 t(12) |  |
| 23  100.21p |  | H-24 |
| 24  34.89p | 2.41 brd(14); 1.64* |  |
| 25  65.26n | 4.04 brs |  |
| 26  39.18p | 1.64*; 1.64* |  |
| 27  61.76p | 5.09 m | H-29 |
| 28  131.48n | 5.41 brdd(10, 11) | H-27 |
| 29  134.12n | 5.41 m | H-27 |
| 30  28.18p | 2.17*; 2.13* |  |
| 31  27.66p | 1.74*; 1.28* |  |
| 32  33.29p | 1.45*; 1.27* |  |
| 33  68.01n | 4.20 brd(9) | H-34a, |
| 34  40.01n | 1.62* | H-34a, H-36, H-35 |
| 34a 11.95n | 0.91 d(7.1) | H-35 |
| 35  72.13n | 3.78 brd(3) | H-34a, H-36 |
| 36  34.20p | 2.02*; 1.68* | H-38, H-35 |
| 37  99.31p |  | H-36, H-38 |
| 38  73.42n | 3.39 brs | H-36, H-40 |
| 39  81.82n | 3.81 brd(9) | H-40a |
| 40  37.74n | 1.98 m | H-38, H-40a, H-39, H-41, |
|  |  | H-42 |
| 40a 12.89n | 0.83 d(6.6) | H-40, H-41 |
| 41  80.59n | 4.85 | H-39, H-40a, H-42 |
| 42  73.74n | 3.15 t(9) | H-41, H-44 |
| 43  79.95n | 3.40 brt(9) | H-42, H-39 |
| 44  40.60p | 2.78*; 2.16* | H-42, H-46 |
| 45  144.01p |  | H-47, H-44, H-46 |
| 45a 116.11p | 4.95 brs; 4.93 brs | H-44, H-46 |
| 46  44.45p | 2.34 dd(7, 14); 2.16* | H-44, H-48 |
| 47  71.67n | 4.28 ddd(6.5, 7, 7) | H-46, H-48, H-49 |
| 48  137.67n | 5.71 dd(6.5, 15) | H-46, H-47, H-50 |
| 49  132.02n | 6.23 brdd(11, 15) | H-47, H-51, H-50 |
| 50  138.01p | 6.33 ddd(11, 11, 17) | H-49, H-51 |
| 51  117.50p | 5.17 brd(17); | H-49 |
|  | 5.04 brd(11) |  |
| OMe  55.90n | 3.33 s | H-21 |
| C-5Ac 172.80p |  | H-OAc |
|     21.63n | 2.03 s |  |

*Coupling constants for these signals are not measured due to overlapping.

The structures of these new compounds compared with spongistatin 1 are shown below:

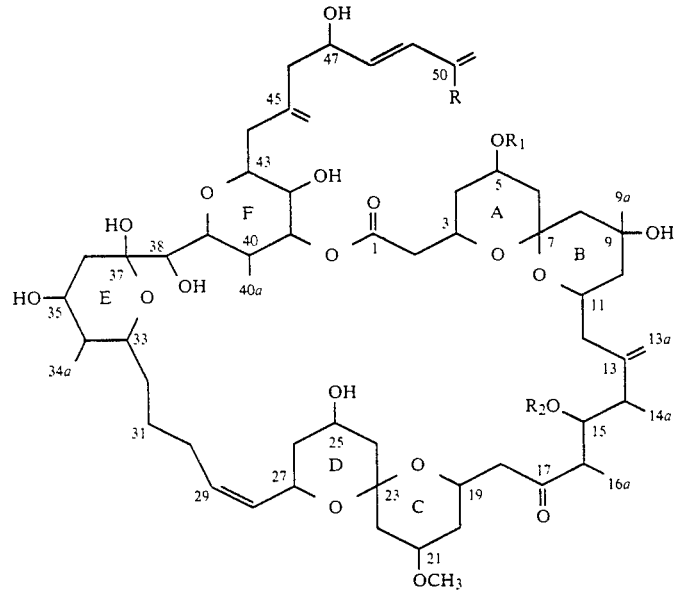

| 1, R = Cl, R$_1$ = R$_2$ = COCH$_3$ | Spongistatin 1 |
| 2, R = H, R$_1$ = R$_2$ = COCH$_3$ | Spongistatin 2 |
| 3, R = Cl, R$_1$ = H, R$_2$ = COCH$_3$ | Spongistatin 3 |
| 4, R = Cl, R$_1$ = COCH$_3$, R$_2$ = H | Spongistatin 4 |
| 5, R = H, R$_1$ = COCH$_3$, R$_2$ = H | Spongistatin 6 |

The NCI cell line panels for spongistatin 1, spongistatin 2, spongistatin 3, spongistatin 4 and spongistatin 6 are shown below in Tables VI, VII, VIII, IX and X, respectively. As can be seen spongistatin 2, spongistatin 3, spongistatin 4 and spongistatin 6 have a relatively high correlation with spongistatin 1. Animal data demonstrated an increased life span (ILS) of 78% at 10 μg/Kg dose for spongistatin 1 and ILS of 55% at 5 μg/kg dose for spongistatin 4, when used to treat implanted tumors on standard experimental animals as shown in Table XII. The high correlations between spongistatin 1, on the one hand, and spongistatin 2, 3, 4 and 6 on the other hand, and other relevant comparison data, are shown in Table XI.

Table VI. Human Tumor Cell Line Evaluation of Spongistatin 1

Table VII. Human Tumor Cell Line Evaluation of Spongistatin 2

Table VIII. Human Tumor Cell Line Evaluation of Spongistatin 3

Table IX. Human Tumor Cell Line Evaluation of Spongistatin 4

Table X. Human Tumor Cell Line Evaluation of Spongistatin 6
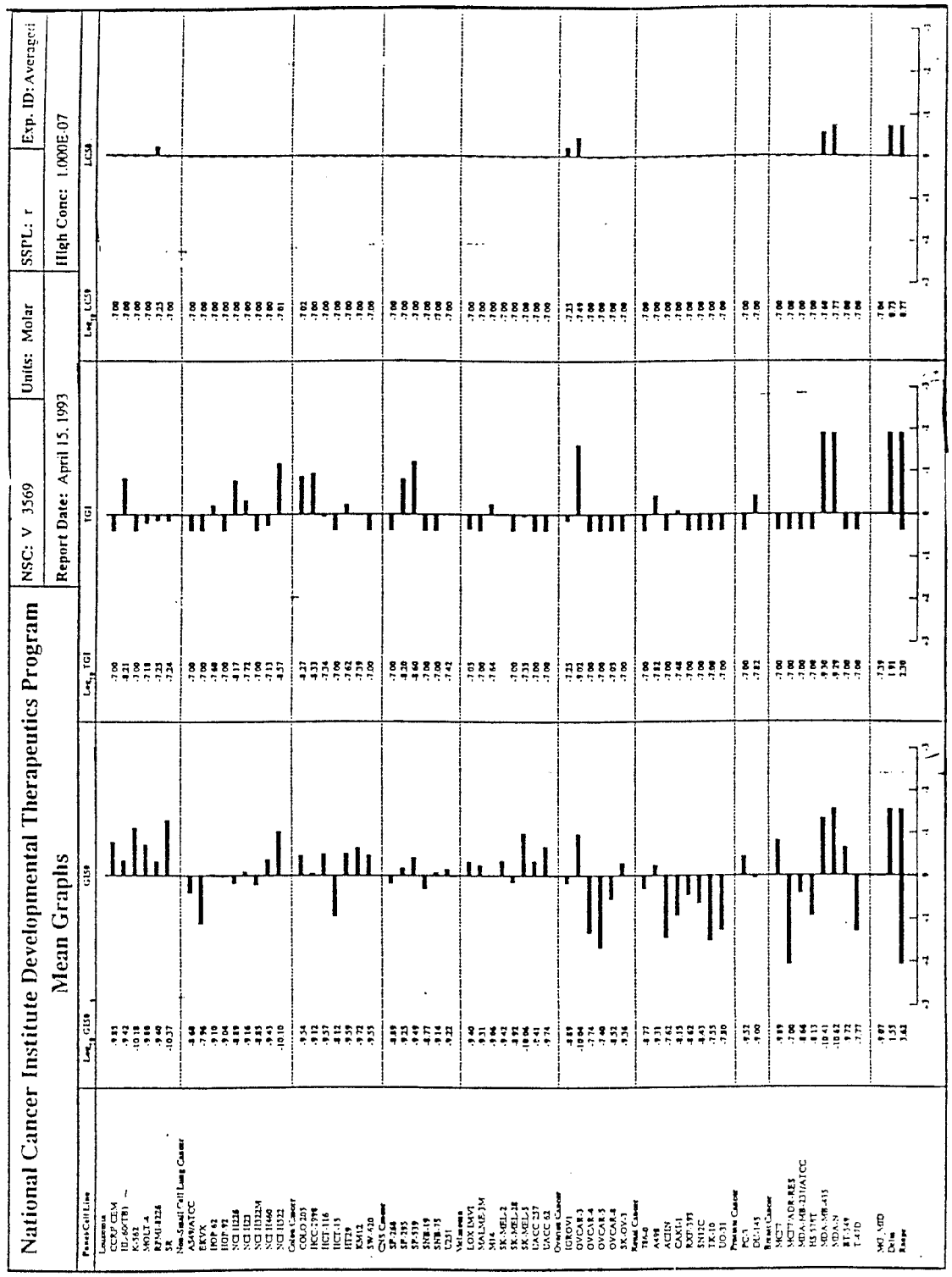

TABLE XI

Results of Comparative Antitumor Evaluations of Spongistatins 1, 2, 3, 4 and 6 in the NCI In Vitro Primary Screen[a]

| Spongistatin Number | Mean Panel GI$_{50}$ ($\times 10^{-10}$M)[b] | Compare Correlation Coefficient[c] |
|---|---|---|
| 1 | 1.17 | 1.00 |
| 2 | 8.51 | 0.83 |
| 3 | 8.32 | 0.90 |
| 4 | 1.02 | 0.93 |
| 6 | 10.7 | 0.86 |

[a]All compounds were tested in quadruplicate at five different concentrations ($10^{-8}$, $10^{-9}$, $10^{-10}$, $10^{-11}$ and $10^{-12}$M) against the entire panel of 60 human tumor cell lines comprising the NCI screen.
[b]Standard errors averaged less than 15% of the respective means.
[c]Correlation coefficients from the Compare pattern-recognition algorithm were calculated by computer using the TGI-centered mean graph profiles of differential cellular sensitivities to 1, 2, 3 and 4. The TGI mean graph profile of 1 was used as the benchmark or "seed" for all of the comparisons.

TABLE XII

| Compound | Anticancer Drug Screening | |
|---|---|---|
| | Dose ($\mu$/Kg/dose) | % ILS |
| Spongistatin 1 | 40.0 | −10 (toxic) |
| | 25.0 | +33 |
| | 10.0 | +72 |
| Spongistatin 4 | 5.0 | +55 |
| Spongistatin 6 | 40.0 | +70 |

Tumor system: P388
Implant: IP, 1.0 E+06 cells
Host: CD2F1, female mice
Median day of death: 10
Schedule: IP, Q 1Dx9(1)
Vehicle: 5% EtOH + distilled water
ILS: % increase in life span over the controls Discovery of the spongistatins in quite distant (in respect to taxonomy and geography) Porifera species suggests that this very important new series of remarkable antineoplastic agents may prove to be widely distributed in such marine invertebrates and/or associated marine microorganisms. Interestingly, a recent first-study of Porifera found adjoining Easter Island, the most remote South Pacific Island, uncovered both *Spirastrella cunctatrix* and *Spongia virgultosa* in the same general area. A future examination of these two sponges for spongistatins should prove useful. Presently we are pursuing extended in vivo human cancer xenograft evaluations of these spongistatins and research directed at completing the absolute configurational assignments for the spongistatins by X-ray crystal structure determinations.

Each of these compounds can also be effectively modified with some or all of the following acids.

(a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropioplic acid and naphthylacetic acid, and the like. Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof. Examples of such substituted hydrocarbon carboxylic acids are: mono-, di-, and trichloroacetic acid; —and —chloropropionic acid;—and—bromobutyric acid;—and—iodovaleric acid; mevalonic acid; 2- and 4-chlorocyclohexanecarboxylic acid; shikimic acid; 2-nitro- 1-methyl-cyclobutanecarboxylic acid; 1,2,3,4,5,6-hexachlorocyclohexanecarboxylic acid; 3-bromo-2-methylcyclohexanecarboxylic acid; 4- and 5-bromo-2-methylcyclohexanecarboxylic acid; 5- and 6-bromo-2-methylcyclohexanecarboxylic acid; 2,3-dibromo-2-methylcyclohexanecarboxylic acid; 2,5-dibromo-2-methylcyclohexanecarboxylic acid; 4,5-dibromo-2-methylcyclohexanecarboxylic acid;5,6-dibromo-2-methylcyclohexanecarboxylic acid; 3-bromo-methylcyclohexanecarboxylic acid; 6-bromo-3-methylcyclohexanecarboxylic acid; 1,6-dibromo-3-methylcyclohexanecarboxylic acid; 2-bromo-4methylcyclohexanecarboxylic acid; 1,2-dibromo-4-methylcyclohexanecarboxylic acid; 3-bromo-2,2,3-trimethylcyclopentanecarboxylic acid; 1-bromo-3,5-dimethylcycohexanecarboxylic acid; homogentisic acid, o-, m-, and p-chlorobenzoic acid; anisic acid; salicylic acid; p-hydroxybenzoic acid; b-resorcylic acid; gallic acid; veratric acid; trimethoxybenzoic acid; trimethoxycinnamic acid; 4,4'-dichlorobenzilic acid; o-, m-, and p-nitrobenzoic acid; cyanoacetic acid; 3,4- and 3,5-dinitrobenzoic acid; 2,4,6-trinitrobenzoic acid; thiocyanoacetic acid; cyanopropionic acid; lactic acid; ethoxyformic acid (ethyl hydrogen carbonate); malic acid; citric acid; isocitric acid; 6-methylsalicyclic acid; mandelic acid, levulinic acid; pyruvic acid; glycine; alanine; valine; isoleucine; leucine; phenylalanine; proline; serine; threonine; tyrosine; hydroxyproline; ornithine; lysine; arginine; histidine; hydroxylysine; phenylglycine; p-aminobenzoic acid; m-aminobenzoic acid; anthranilic acid; aspartic acid; glutamic acid; aminoadipic acid; glutamine; asparagine; and the like.

The administration of spongistatins 1, 2, 3, and 4 and their pharmaceutically active, physiologically compatible derivatives is useful for treating animals or humans afflicted with a neoplastic disease, such as, for example, acute myelocytic leukemia, acute lymphocytic leukemia, malignant melanoma, adenocarcinoma of lung, neuroblastoma, small cell carcinoma of lung, breast carcinoma, colon carcinoma, gastric carcinoma, ovarian carcinoma, bladder carcinoma, hematologic malignancies and the like.

The dosage administered will be dependent upon the identity of the neoplastic disease; the type of host involved, including its age, health and weight; the kind of concurrent treatment, if any; the frequency of treatment and therapeutic ratio.

Illustratively, dosage levels of the administered active ingredients are: intravenous, 0.1 to about 40 µg/kg; intramuscular, 1 to about 50 µg/kg; orally, 5 to about 100 µg/kg; intranasal instillation, 5 to about 100 µg/kg; and aerosol, 5 to about 100 µg/kg. As used herein, µg/kg means weight of active ingredient in micrograms divided by the body weight of the host in kilograms.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; and for parenteral use in a concentration of from about 0.05 to about 50% w/w of the composition and preferably from about 5 to about 20% w/w.

The composition of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling the mixture into formed gelatin sheaths. As an adjuvant to the filling operation, a lubricant such as a talc, magnesium stearate, calcium stearate and the like can be added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

When desired, each tablet can be provided with a protective coating consisting of a sealing coat or enteric coat of shellac, a coating of sugar and methylcellulose and a polish coating of carnauba wax. Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization can not be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably pyrogen free ("P.E.") water. A dry powder can be formulated when insufflation is the administration of choice.

For use as aerosols, the active ingredients can be packaged in a pressurized aerosol container together with a gaseous or liquefied propellant, for example, dichlorodifluoromethane, carbon dioxide, nitrogen, propane, and the like, with the usual adjuvants such a cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antineoplastic agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof.

EXAMPLE I

Several dosage forms can be prepared embodying the present invention. They are shown in the following examples which the notation "active ingredient" signifies spongistatin 1, 2, 3, 4, and 6, their synthetic counterparts and the non-toxic pharmaceutically active derivatives thereof.

COMPOSITION "A"

Hard-Gelatin Capsules

One thousand two-piece hard gelatin capsules for oral use, each capsule containing 20 µg of an active ingredient are prepared from the following types and amounts of ingredients:

| Active ingredient, micronized | 20 mg |
|---|---|
| Corn Starch | 20 gm |
| Talc | 20 gm |
| Magnesium stearate | 2 gm |

The active ingredient, finely divided by means of an air micronizer, is added to the other finely powdered ingredients, mixed thoroughly and then encapsulated in the usual manner.

The foregoing capsules are useful for treating a neoplastic disease by the oral administration of one or two capsules one to four times a day.

Using the procedure above, capsules are similarly prepared containing an active ingredient in 5, 25 and 50 µg amounts by substituting 5 µm, 25 µm and 50 µm of an active ingredient for the 20 µm used above.

COMPOSITION "B"

Soft Gelatin Capsules

One-piece soft gelatin capsules for oral use, each containing 20 µg of an active ingredient (finely divided by means of an air micronizer), are prepared by first suspending the compound in 0.5 ml of corn oil to render the material capsulatable and then encapsulating in the above manner.

The foregoing capsules are useful for treating a neoplastic disease by the oral administration of one or two capsules one to four times a day.

COMPOSITION "C"

Tablets

One thousand tablets, each containing 20 µg of an active ingredient are prepared from the following types and amounts of ingredients.

| Active ingredient micronized | 20 mg |
|---|---|
| Lactose | 300 gm |
| Corn starch | 50 gm |
| Magnesium stearate | 4 gm |
| Light liquid petrolatum | 5 gm |

The active ingredient finely divided by means of an air micronizer, is added to the other ingredients and then thoroughly mixed and slugged. The slugs are broken down by forcing through a Number Sixteen screen. The resulting granules are then compressed into tablets, each tablet containing 20 µg of the active ingredient.

The foregoing tablets are useful for treating a neoplastic disease by the oral administration of one or two tablets one to four times a day.

Using the procedure above, tablets are similarly prepared containing an active ingredient in 25 µg and 10 µg amounts by substituting 25 mg and 10 mg of an active ingredient for the 20 µm used above.

COMPOSITION "D"

Oral Suspension

One thousand ml of an aqueous suspension for oral use, containing in each teaspoonful (5 ml) dose, 5 µg of an active ingredient, is prepared from the following types and amounts of ingredients:

| Active ingredient micronized | 5 mg |
|---|---|
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml | |

The citric acid, benzoic acid, sucrose, tragacanth and lemon oil are dispersed in sufficient water to make 850 ml of suspension. The active ingredient finely divided by means of an air micronizer, is stirred into the syrup until uniformly distributed. Sufficient water is added to make 1000 ml.

The composition so prepared is useful for treating a neoplastic disease at a dose of 1 tablespoonful (15 ml) three times a day.

COMPOSITION "E"

Parenteral Product

A sterile aqueous suspension for parenteral injection, containing in 1 ml, 30 µg of an active ingredient for treating a neoplastic disease, is prepared from the following types and amounts of ingredients:

| Active ingredient, micronized | 30 mg |
|---|---|
| Polysorbate 80 | 5 gm |
| Methylparaben | 2.5 gm |
| Propylparaben | 0.17 gm |
| Water for injection, q.s. 1000 ml | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a neoplastic disease at a dose of 1 milliliter (1 mL) three times a day.

COMPOSITION "F"

Suppository, Rectal and Vaginal

One thousand suppositories, each weighing 2.5 gm and containing 20 µg of an active ingredient are prepared from the following types and amounts of ingredients:

| Active ingredient, micronized | 20 mg |
|---|---|

-continued

| | |
|---|---|
| Propylene glycol | 150 gm |
| Polyethylene glycol #4000, q.s. | 1,500 gm |

The active ingredient is finely divided by means of an air micronizer and added to the propylene glycol and the mixture passed through a colloid mill until uniformly dispersed. The polyethylene glycol is melted and the propylene glycol dispersion added slowly with stirring. The suspension is poured into unchilled molds at 40° C. The composition is allowed to cool and solidify and then removed from the mold and each suppository is foil wrapped.

The foregoing suppositories are inserted rectally or vaginally for treating a neoplastic disease.

COMPOSITION "G"

Intranasal Suspension

One thousand ml of a sterile aqueous suspension for intranasal instillation is prepared, containing 20 µg of an active ingredient per ml of suspension, from the following types and amounts of ingredients:

| | |
|---|---|
| Active ingredient, micronized | 20 mg |
| Polysorbate 80 | 5 gm |
| Methylparaben | 2.5 gm |
| Propylparaben | 0.17 gm |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a neoplastic disease, by intranasal instillation of 0.2 to 0.5 ml given one to four times a day.

An active ingredient can also be present in the undiluted pure form for use locally about the cutis, intranasally, pharyngolaryngeally, bronchially, or orally.

COMPOSITION "H"

Powder

Five mg of an active ingredient in bulk form is finely divided by means of an air micronizer. The micronized powder is placed in a shaker-type container.

The foregoing composition is useful for treating a neoplastic disease, at localized sites by applying a powder one to four times per day.

COMPOSITION "I"

Oral Powder

Ten mg of an active ingredient in bulk form is finely divided by means of an air micronizer. The micronized powder is divided into individual doses of 20 µg and packaged.

The foregoing powders are useful for treating a neoplastic disease, by the oral administration of one or two powders suspended in a glass of water, one to four times per day.

COMPOSITION "J"

Insufflation

Ten mg of an active ingredient in bulk form is finely divided by means of an air micronizer.

The foregoing composition is useful for treating a neoplastic disease, by the inhalation of 30 µg one to four times per day.

COMPOSITION "K"

Hard Gelatin Capsules

One hundred two-piece hard gelatin capsules for oral use, each capsule containing 20 µg of an active ingredient.

The active ingredient is finely divided by means of an air micronizer and encapsulated in the usual manner.

The foregoing capsules are useful for treating a neoplastic disease, by the oral administration of one or two capsules, one to four times a day.

Using the procedure above, capsules are similarly prepared containing active ingredient in 5, 25 and 50 µg amounts by substituting 5 mg, 25 mg and 50 mg of the active ingredient for the 20 mg used above.

From the foregoing it is apparent that a new and useful invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended herein.

Accordingly, what is claimed is:

1. A composition of matter having the following structure:

[chemical structure diagram]

wherein R is selected from the group consisting of Cl and H, $R_1$ is selected from the group consisting of H and $COCH_3$, $R_2$ is selected from the group consisting of H and $COCH_3$, provided that if R=Cl, then $R_1$ and $R_2$ are not both $COCH_3$.

2. A purified composition of matter according to claim 1 wherein the concentration of said composition needed to attain an $ED_{50}$ under the P388 system is less than about $1.0 \times 10^1$ mg/ml.

3. A purified composition of matter according to claim 1 wherein the concentration of said composition needed to attain an $ED_{50}$ under the P388 system is less than $1.0 \times 10^1$ µg/ml.

4. A purified composition of matter according to claim 1 wherein the concentration of said composition needed to attain on $ED_{50}$ under the P388 system is less than $1.0 \times 10^{-1}$ μg/ml.

5. A purified composition of matter according to claim 1 wherein the concentration of said composition needed to attain an $ED_{50}$ under the P388 system is less than $1.0 \times 10^{-3}$ μg/ml.

6. A composition of matter according to claim 1 wherein R=H, and $R_1$=COCH$_3$ and $R_2$=COCH$_3$ herein denominated as "spongistatin 2".

7. A composition of matter according to claim 1 wherein R=Cl $R_1$=H and $R_2$=COCH$_3$, herein denominated as "spongistatin 3".

8. A composition of matter according to claim 1 wherein R=Cl, $R_1$=COCH$_3$, and $R_2$=H herein denominated as "spongistatin 4".

9. A composition of matter according to claim 1 wherein R=H, $R_1$=COCH$_3$, and $R_2$=H herein denominated as "spongistatin 6".

* * * * *